US010545102B2

(12) United States Patent
Takahashi et al.

(10) Patent No.: US 10,545,102 B2
(45) Date of Patent: Jan. 28, 2020

(54) COORDINATE ALIGNMENT TOOL FOR COORDINATE MEASURING DEVICE AND MEASURING X-RAY CT APPARATUS

(71) Applicant: MITUTOYO CORPORATION, Kanagawa (JP)

(72) Inventors: Akihito Takahashi, Kawasaki (JP); Seiji Sasaki, Kawasaki (JP)

(73) Assignee: MITUTOYO CORPORATION, Kanagawa (JP)

( * ) Notice: Subject to any disclaimer, the term of this patent is extended or adjusted under 35 U.S.C. 154(b) by 255 days.

(21) Appl. No.: 15/800,408

(22) Filed: Nov. 1, 2017

(65) Prior Publication Data

US 2018/0120242 A1 May 3, 2018

(30) Foreign Application Priority Data

Nov. 2, 2016 (JP) .................................. 2016-215672

(51) Int. Cl.
*G01N 23/046* (2018.01)

(52) U.S. Cl.
CPC ..... *G01N 23/046* (2013.01); *G01N 2223/303* (2013.01); *G01N 2223/419* (2013.01)

(58) Field of Classification Search
CPC ........... G01N 23/046; G01N 2223/303; G01N 2223/419
See application file for complete search history.

(56) References Cited

U.S. PATENT DOCUMENTS

| 6,038,282 A * | 3/2000 | Wiesent ............... A61B 6/4441 378/4 |
| 6,359,960 B1 * | 3/2002 | Wahl ....................... G06T 7/70 378/20 |
| 7,056,019 B1 * | 6/2006 | Hanson .................. A61B 6/583 378/18 |
| 8,104,958 B2 * | 1/2012 | Weiser ................... A61B 6/583 378/162 |
| 8,777,485 B2 * | 7/2014 | Holt .......................... A61B 6/03 250/252.1 |
| 8,804,905 B2 | 8/2014 | Christoph et al. |
| 8,845,191 B2 * | 9/2014 | Ngar .................... A61N 5/1075 378/18 |
| 2009/0116621 A1 * | 5/2009 | Yuan ...................... A61B 6/583 378/207 |
| 2011/0071389 A1 * | 3/2011 | Simon ..................... A61B 6/12 600/426 |
| 2011/0262024 A1 * | 10/2011 | Bulitta .................. A61B 6/583 382/132 |

(Continued)

FOREIGN PATENT DOCUMENTS

| JP | 2002-055062 A | 2/2002 |
| JP | 2002-071345 A | 3/2002 |

(Continued)

*Primary Examiner* — Edwin C Gunberg
(74) *Attorney, Agent, or Firm* — Greenblum & Bernstein, P.L.C.

(57) ABSTRACT

A coordinate alignment tool includes a base having at least two ground faces to hold an attitude suitable for measurement by a coordinate measuring device and an attitude suitable for measurement by a measuring X-ray CT apparatus, and a fixer to fixate a measured object to the base; and at least three master balls arranged on the base.

7 Claims, 5 Drawing Sheets

Tool alone (56) References Cited

U.S. PATENT DOCUMENTS

2013/0215114 A1\* 8/2013 Cherkashin ............ A61B 6/584
 345/420
2018/0120242 A1\* 5/2018 Takahashi ............. G06T 11/008
2019/0209080 A1\* 7/2019 Gullotti ................ A61B 5/1072

FOREIGN PATENT DOCUMENTS

| JP | 3427046 B2 | 7/2003 |
|----|------------|--------|
| JP | 2004-012407 A | 1/2004 |
| JP | 5408873 B2 | 2/2014 |

\* cited by examiner

Fig. 3A: Tool alone

Fig. 3B: Work piece mounted

Fig. 3C: Measuring attitude for coordinate measuring device

Fig. 3D: Measuring attitude for measuring X-ray CT apparatus

COORDINATE ALIGNMENT TOOL FOR COORDINATE MEASURING DEVICE AND MEASURING X-RAY CT APPARATUS

CROSS-REFERENCE TO RELATED APPLICATIONS

The present application claims priority under 35 U.S.C. § 119 of Japanese Application No. 2016-215672, filed on Nov. 2, 2016, the disclosure of which is expressly incorporated by reference herein in its entirety.

BACKGROUND OF THE INVENTION

1. Field of the Invention

The present invention relates to a coordinate alignment tool for a measuring X-ray CT apparatus and a coordinate measuring device. In particular, the present invention relates to a coordinate alignment tool for a measuring X-ray CT apparatus and a coordinate measuring device where the coordinate alignment tool enables coordinates for measurement data acquired by a three-dimensional coordinate measuring device (hereafter, referred to as a coordinate measuring device) and measurement data acquired by the measuring X-ray CT apparatus to be aligned easily, and where the coordinate alignment tool enables efficient measurement of external dimensions and internal dimensions with high accuracy.

2. Description of Related Art

Medical X-ray CT apparatuses were brought into practical use in the 1970s, and based on this technology, X-ray CT apparatuses for industrial products came out around the early 1980s. Since then, the industrial X-ray CT apparatuses have been used for observation and inspection of pores in improperly cast metal components, a welding issue of a welded component, a circuit pattern defect of an electronic circuit component, and the like, which are difficult to check from an external view. Meanwhile, along with a recent spread of 3D printers, demand is growing not only for the observation and the inspection of the interior of work pieces created by 3D printers, but also for 3D dimension measurement of an internal configuration and for accuracy thereof.

With respect to the above-mentioned trends in the technology, the measuring X-ray CT apparatus is spreading in areas centering on Germany (See Japanese Patent Laid-open Publication Nos. 2002-71345 and 2004-12407). In the measuring X-ray CT apparatus, a measured object is placed at the center of a rotation table and X-ray irradiation is performed while rotating the measured object.

Figure 1:
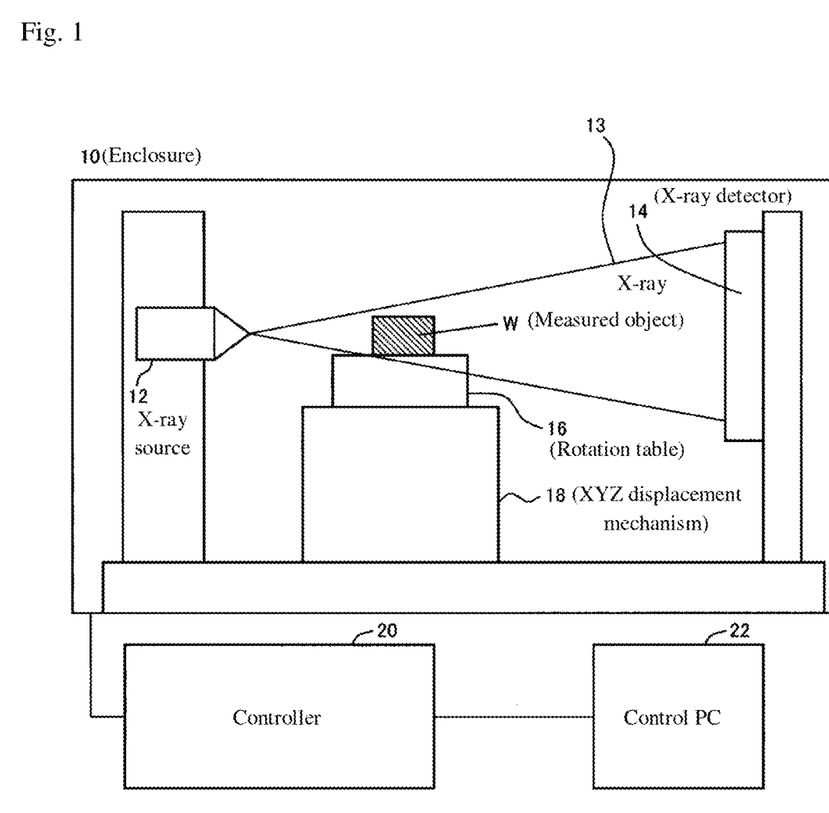
FIG. 1 illustrates a cross section of an overall configuration of a generic X-ray CT apparatus used for measurement.

A configuration of a generic X-ray CT apparatus 1 which is used for measurement is shown in FIG. 1. The X-ray CT apparatus 1 is configured with an enclosure 10 which shields X-rays, a controller 20, a control PC 22, and the like. The enclosure 10 includes therein: an X-ray source 12 firing X-rays 13 (shaped in a cone beam), an X-ray detector 14 detecting the X-rays 13, a rotation table 16 on which a measured object W is placed and which rotates the measured object W for CT imaging, and an XYZ displacement mechanism 18 adjusting a position or magnification of the measured object W which is projected onto the X-ray detector 14. The controller 20 controls the devices mentioned above, and the control PC 22 issues instructions from a user to the controller 20.

In addition to controlling each device, the control PC 22 includes a function to display a projection image of the measured object W which is projected onto the X-ray detector 14, and a function to reconfigure a tomographic image from a plurality of projection images of the measured object W.

Figure 2:
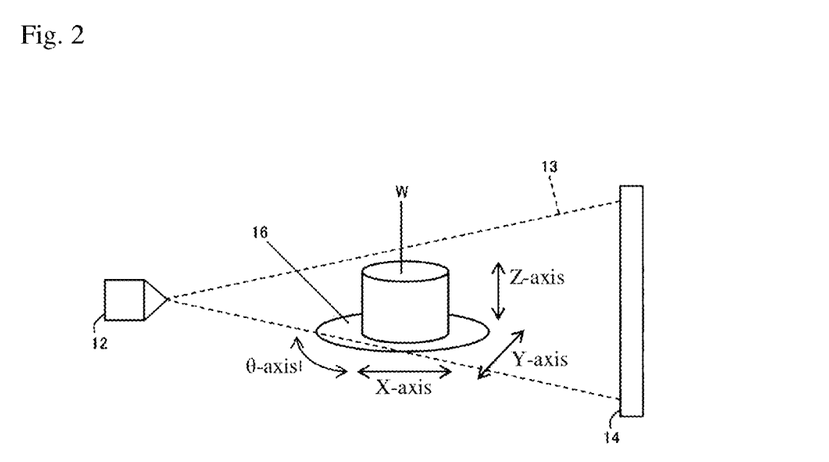
FIG. 2 illustrates a perspective view showing an arrangement of a main portion of the generic X-ray CT apparatus used for measurement.

As shown in FIG. 2, the X-rays 13 fired from the X-ray source 12 reach the X-ray detector 14 by passing through the measured object W on the rotation table 16. The tomographic image of the measured object W is generated by obtaining, using the X-ray detector 14, transmission images (projection images) of the measured object W in various directions while rotating the measured object W and by reconfiguring the images using a reconfiguration algorithm, such as a back projection method, a successive approximation method, and the like.

By controlling XYZ axes of the XYZ displacement mechanism 18 and a θ axis of the rotation table 16, the position of the measured object W can be displaced and an image capture range (position, magnification ratio) or an image capture angle of the measured object W can be adjusted.

While the measuring X-ray CT apparatus, which obtains the non-destructive tomographic image of the measured object, can measure the internal configuration, the measurement of the external dimensions of the measured object does not reach the accuracy of a coordinate measuring device.

Therefore, in order to meet a demand to be more accurate for the dimension measurement, a composite measurement system has been proposed in which the coordinate measuring device is installed inside the X-ray CT apparatus (Japanese Patent No. 5408873 ([0084] and FIG. 8)) or in a vicinity of the X-ray CT apparatus (Japanese Patent No. 3427046). In the composite measurement system, 3D dimensions obtained by the X-ray CT apparatus have been calibrated based on the external dimensions obtained with a measurement using the coordinate measuring device to achieve high accuracy.

Japanese Patent 5408873 ([0084] and FIG. 8) describes that a reference 50 is placed on a rotation table 60 and calibration is performed, and Japanese Patent Laid-open Publication No. 2002-55062 (claim 1, [0012], and FIG. 1) describes that a sample base 10 with a calibrating jig is mounted on a rotation table 3a, and a sample 11 is set in the center.

However, as described in Japanese Patent No. 5408873 ([0084] and FIG. 8), when the coordinate measuring device is mounted inside the measuring X-ray CT apparatus while still attempting to provide sufficient functions of the coordinate measuring device, an overall size of the apparatus increases and the mass of a lead enclosure which blocks the X-rays increases. Further, there are issues such as the necessity of taking measures to block the X-rays from reaching the coordinate measuring device or a probe.

On the other hand, when the functions of the coordinate measuring device are limited and the device is mounted, the above-noted measures can be taken, however, the range of measured objects which can be measured with high accuracy ends up decreasing.

In addition, it is necessary to conduct the measurements using the coordinate measuring device and the X-ray CT apparatus successively, and therefore, while the one is operating, the other is stopped. Accordingly, the coordinate measuring device and the X-ray CT apparatus, which are both expensive, cannot be used at the same time. This affects work efficiency, especially when the continuous measurement of mass produced work pieces is necessary.

On the other hand, when the coordinate measuring device and the X-ray CT apparatus are placed separately, both devices can be effectively used independently. However, the coordinates of both sets of measurement data need to be aligned so as to match up.

Japanese Patent No. 5408873 ([0084] and FIG. 8) and Japanese Patent Laid-open Publication No 2002-55062 (claim 1, [0012], and FIG. 1) are both for calibrating a deviation of the rotation center position of the rotation table, and are not for aligning the coordinates of the measurement data acquired by the measuring X-ray CT apparatus and the coordinates of the measurement data acquired by the coordinate measuring device.

The present invention has been conceived in order to resolve the above-noted conventional issues, and enables easy alignment of the coordinates of the measurement data acquired by the measuring X-ray CT apparatus and the coordinates of the measurement data acquired by the coordinate measuring device, and allows a highly accurate measurement of the external dimensions and the internal dimensions to be performed efficiently.

SUMMARY OF THE INVENTION

In order to solve the above-noted issues, the present invention provides a base and a fixer. The base has at least two ground faces to hold an attitude suitable for measurement by a coordinate measuring device and an attitude suitable for measurement by a measuring X-ray CT apparatus. The fixer fixates a measured object to the base.

In this example, the attitude suitable for measurement by the coordinate measuring device can be an attitude which matches a reference plane of the coordinate measuring device and a reference plane of the measured object.

Further, the attitude suitable for measurement by the measuring X-ray CT apparatus can be an inclined attitude which facilitates obtaining an X-ray transmission image.

In addition, at least three master balls arranged on the base can be further provided.

Furthermore, the fixer can be a chuck, an adhesive, or a double-sided adhesive tape.

Because the coordinates of the measured object are determined by the coordinate alignment tool according to the present invention, it becomes possible to take measurements at the same coordinates with the measuring X-ray CT apparatus and the coordinate measuring device. Therefore, highly accurate measurement data that is a product of the full functionality and performance of the coordinate measuring device, which is arranged separately from the measuring X-ray CT apparatus, may be aligned with measurement data acquired by the measuring X-ray CT apparatus when used, and therefore highly accurate measurement of external dimensions and internal dimensions is possible. In particular, when the master balls are provided, by assigning values to the dimensions between the balls, it is possible to simultaneously calibrate a magnification of the measuring X-ray CT apparatus.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIGS. 3A to 3D illustrate a first embodiment of a coordinate alignment tool according to the present invention, where

DETAILED DESCRIPTION OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the forms of the present invention may be embodied in practice.

Hereafter, embodiments of the present invention are described in detail with reference to the drawings. Moreover, the present invention is not limited by the content described in the embodiments and examples that follow. Additionally, elements easily conceivable to a person skilled in the art and elements that are intrinsic equivalents or otherwise equal in scope are included within the compositional requirements of the examples and the embodiments below. Furthermore, the disclosed compositional requirements within the written embodiments and examples below may be combined or selectively employed as appropriate.

As shown in FIGS. 3A to 3D, a coordinate alignment tool 50 in a first embodiment according to the present invention includes a base 52, a chuck 54, and three master balls 58A, 58B, and 58C. The base 52 has a three-pronged shape and includes four ground faces 52A, 52B, 52C, and 52D to hold (i.e., maintain or position) (C) the base at an attitude suitable for measurement by a coordinate measuring device, and (D) an attitude suitable for measurement by a measuring X-ray CT apparatus. The chuck 54 fixes a measured object W to the base 52. The three master balls 58A, 58B, and 58C, having different heights from each other, are arranged respectively on poles 56A, 56B, and 56C which are on arms of the base 52 extending in three directions.

Figures 3A, 3B:
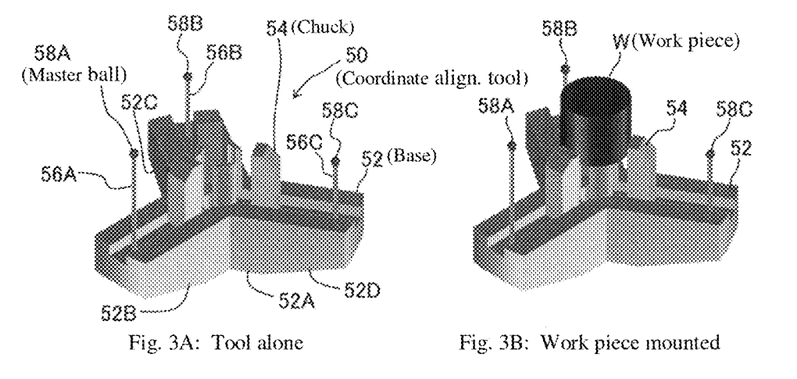
FIG. 3A illustrates a perspective view of a configuration of the tool alone.
FIG. 3B illustrates a perspective view of a state where a work piece is mounted.

At a center bottom portion of the base 52, the horizontal ground face 52A, which is parallel to a bottom face of the work piece W, for example, is formed to take a horizontal attitude which is suitable for measurement by the coordinate measuring device.

The base 52 further includes the arms extending in three directions, and the bottom faces of the respective arms are formed with the inclined ground faces 52B, 52C, and 52D to take the attitude suitable for measurement by the measuring X-ray CT apparatus, and also the poles 56A, 56B, and 56C are planted respectively into each arm and the master balls 58A, 58B, and 58C are arranged at the top thereof, respectively.

Inclination angles of the ground faces 52B, 52C, and 52D can be changed according to the measured object W, such as having all three angles be the same or having a different angle for each arm. Alternatively, the ground face 52A can be extended and the ground faces 52C and 52D can be omitted.

By changing the heights at which all of the master balls 58A, 58B, and 58C, are arranged, a coordinate system can be determined with high accuracy. Moreover, two or three heights of the master balls can be the same.

The base 52 and the chuck 54 are preferably configured by a material that transmits X-rays.

Figure 4:
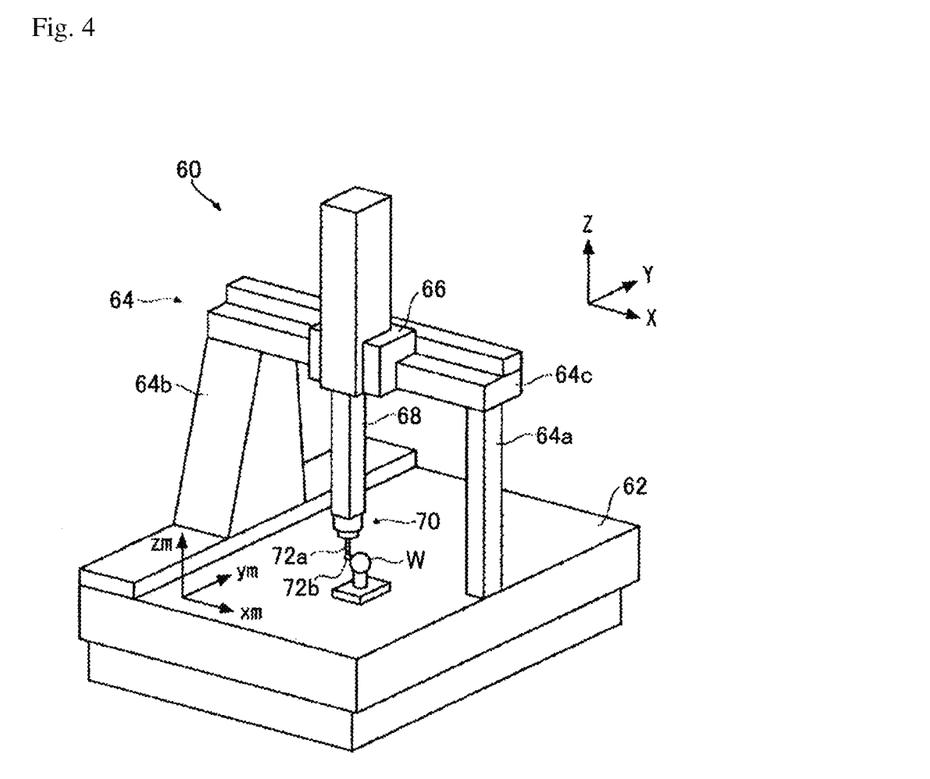
FIG. 4 illustrates a perspective view of an exemplary coordinate measuring apparatus which can be used in the present invention.

In a state where a work piece W (measured object) is mounted on the coordinate alignment tool 50, as shown in FIG. 3B, the coordinate alignment tool 50 is arranged for use on a rotation table 16 of the measuring X-ray CT apparatus (shown in FIGS. 1 and 2) or on a surface plate 62 of a coordinate measuring device 60 (illustrated by an example in FIG. 4).

The coordinate measuring device 60 includes the surface plate 62 (reference plane); a portal frame 64 having a pair of columns 64a and 64b which are movable on the surface plate 62 in a front-back direction (Y axis direction) and a beam 64c bridging over the columns 64a and 64b; a movable column 66 which moves on the beam 64c of the portal frame 64 in a left-right direction (X axis direction); a movable slider 68 which moves on the column 66 in a vertical direction (Z axis direction); a probe 70 fixated to a bottom end of the slider 68; and a stylus 72a and, for example, a spherical measuring probe 72b which are fixated to a tip (lower end in the drawing) of the probe 70.

In this embodiment, with the work piece W fixated to the coordinate alignment tool 50, the coordinates of the work piece W relative to the coordinate alignment tool 50 are determined using the three master balls 58A, 58B, and 58C. In this way, the coordinates of the work piece W are determined, and therefore, measurement at the same coordinates is possible on the different apparatuses.

Figure 3C:
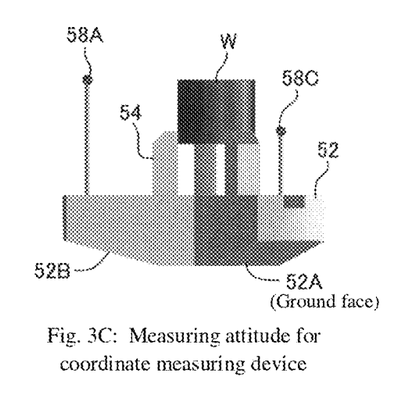
FIG. 3C illustrates a side view of a measuring attitude for a coordinate measuring device.
Figure 3D:
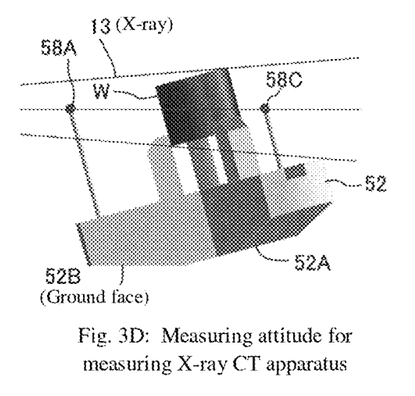
FIG. 3D illustrates a side view of a measuring attitude for a measuring X-ray CT apparatus.
Figure 5:
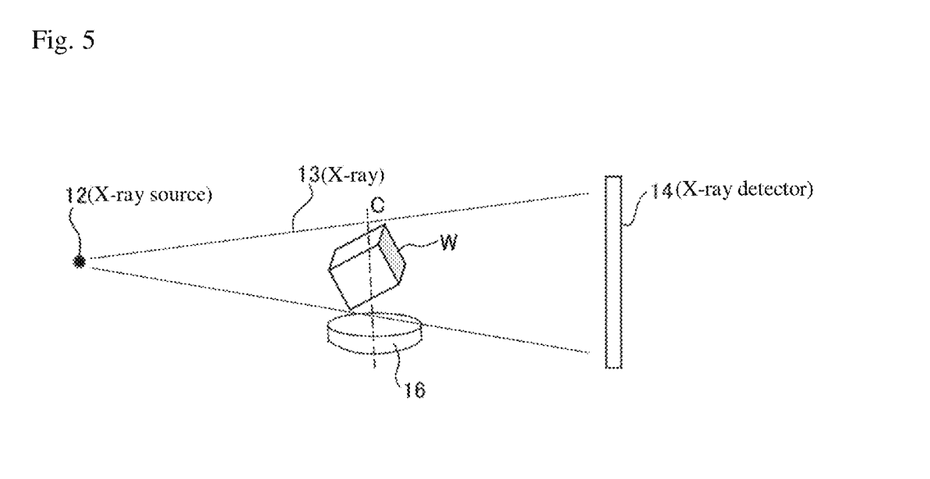
FIG. 5 illustrates a side view of an attitude which facilitates measurement with the measuring X-ray CT apparatus.

When measuring with the coordinate measuring device, in order to measure with high accuracy, horizontal deployment (as shown in FIG. 3C) can be used to allow measurement in the attitude (horizontal attitude, for example) aligning with the coordinate axes of the measuring device. On the other hand, when measuring with the measuring X-ray CT apparatus, deployment at an angle (as shown in FIG. 3D) can be used to allow measurement in the attitude (inclined attitude) which facilitates obtaining an X-ray transmission image. In this example, the attitude which facilitates measurement with the measuring X-ray CT apparatus, as shown in FIG. 5, is a state where no face is perpendicular to the rotation axis C of the rotation table 16. Accordingly, measurements can be performed in the attitude suitable for each measuring device.

Figure 6:
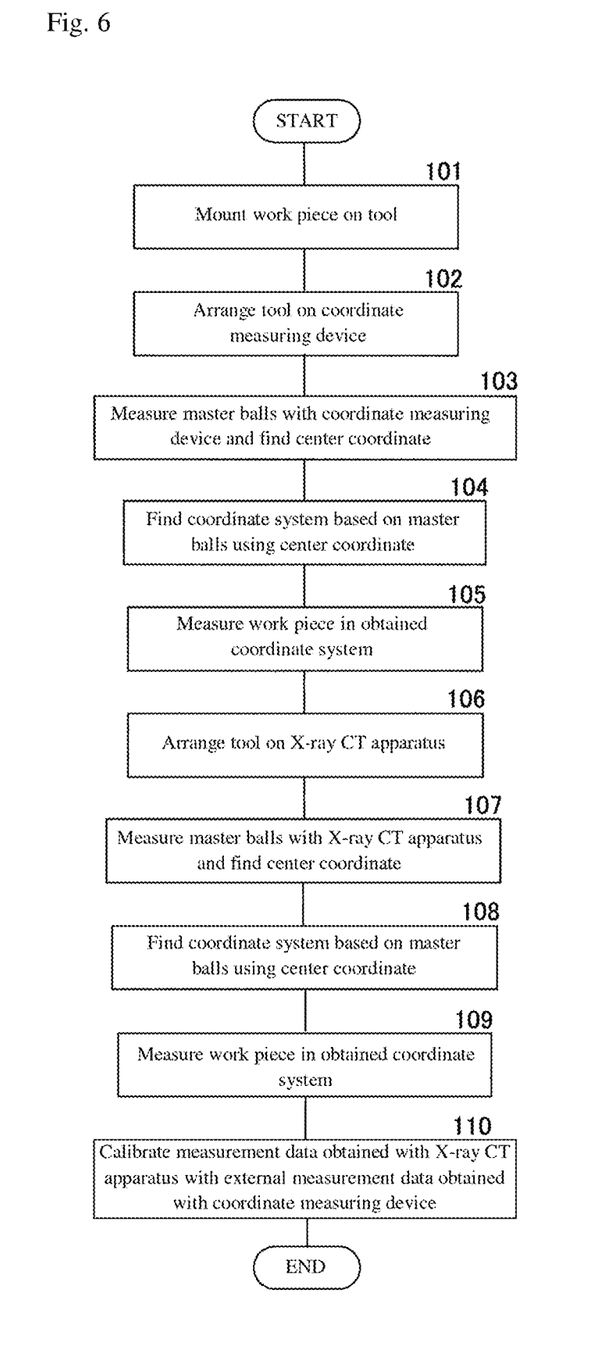
FIG. 6 is a flow chart illustrating a process of measurement using the first embodiment.

Measurement procedures are described in detail with reference to FIG. 6 below.

First, the work piece W is mounted onto the coordinate alignment tool 50 and fixated with the chuck 54 in step 101.

In step 102, the coordinate alignment tool 50 is arranged on the surface plate 62 of the coordinate measuring device 60 in the attitude which facilitates measurement (horizontal attitude shown in FIG. 3C, for example) with the coordinate measuring device 60.

Then, in step 103, the three master balls 58A, 58B, and 58C are measured with the coordinate measuring device 60 and a center coordinate is found.

Figure 7:
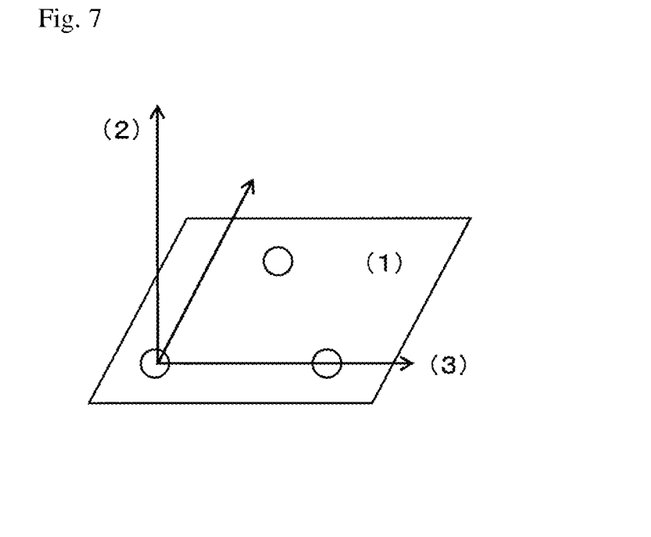
FIG. 7 illustrates a perspective view of a method to obtain a coordinate system based on master balls from a center coordinate.

Next, proceeding to step 104, a coordinate system based on the master balls is found using the center coordinate. Specifically, as shown in FIG. 7, (1) a plane can be generated using three points, (2) a line perpendicular to the plane can be generated using the plane and a single point, and (3) a line horizontal to the plane can be found using the two points.

Then, in step 105, the work piece W is measured in the obtained coordinate system.

In step 106, the coordinate alignment tool 50 is arranged on the rotation table 16 of the measuring X-ray CT apparatus in the attitude which facilitates measurement (inclined attitude shown in FIG. 3D, for example) with the measuring X-ray CT apparatus.

Then, in step 107, the three master balls 58A, 58B, and 58C are measured with the measuring X-ray CT apparatus and the center coordinate is found.

Next, in step 108, a coordinate system based on the master balls is found using the center coordinate in the same way as step 104.

Then, in step 109, the work piece W is measured in the obtained coordinate system.

Next, proceeding to step 110, final measurement data is obtained by calibrating the measurement data of the X-ray CT apparatus obtained in step 109 with external measurement data of the coordinate measuring device obtained in step 105.

In this way, highly accurate measurement can be performed by calibrating the measurement data obtained with the X-ray CT apparatus using the external measurement data obtained with the coordinate measuring device.

Figure 8:
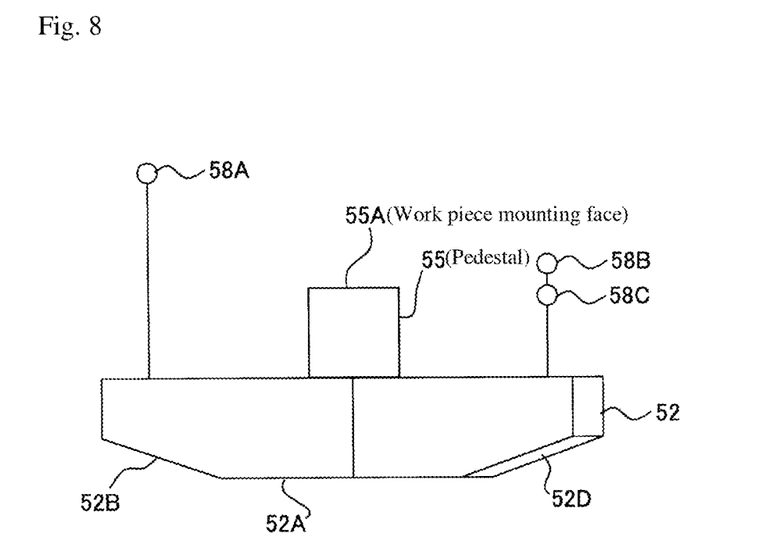
FIG. 8 illustrates a side view of a second embodiment of a coordinate alignment tool according to the present invention.

According to this embodiment, the work piece W can easily be fixated with the chuck 54. Moreover, a method to fixate the work piece W onto the coordinate alignment tool 50 is not limited to this. As shown in a second embodiment in FIG. 8, instead of the chuck 54, a pedestal 55 is provided to the coordinate alignment tool 50 and the work piece W may be fixated to a work piece mounting face 55A of the pedestal 55 with an adhesive, a double-sided adhesive tape, or the like.

In addition, the shape of the base 52 is not limited to the shape having three separating arms.

When it is possible to align the coordinate systems using the work piece W alone, the master balls can be omitted as long as the work piece W can be arranged in attitudes suitable for the coordinate measuring device and the measuring X-ray CT apparatus.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to be limited to the particulars disclosed herein; rather, the present invention extends to all functionally equivalent structures, methods and uses, such as are within the scope of the appended claims.

The present invention is not limited to the above described embodiments, and various variations and modifications may be possible without departing from the scope of the present invention.

What is claimed is:

1. A coordinate alignment tool for a measuring X-ray CT apparatus and a coordinate measuring device, comprising:
   a base having at least two ground faces to hold the base at:
      an attitude for measurement by the coordinate measuring device, and
      an attitude for measurement by the measuring X-ray CT apparatus; and
   a fixer configured to fix a measured object to the base.

2. The coordinate alignment tool for the measuring X-ray CT apparatus and the coordinate measuring device according to claim 1, wherein the attitude for measurement by the coordinate measuring device is an attitude which matches a reference plane of the coordinate measuring device and a reference plane of the measured object.

3. The coordinate alignment tool for the measuring X-ray CT apparatus and the coordinate measuring device according to claim 1, wherein the attitude for measurement by the measuring X-ray CT apparatus is an inclined attitude which facilitates obtaining an X-ray transmission image.

4. The coordinate alignment tool for the measuring X-ray CT apparatus and the coordinate measuring device according to claim 1, further comprising at least three master balls arranged on the base.

5. The coordinate alignment tool for the measuring X-ray CT apparatus and the coordinate measuring device according to claim 2, further comprising at least three master balls arranged on the base.

6. The coordinate alignment tool for the measuring X-ray CT apparatus and the coordinate measuring device according to claim 3, further comprising at least three master balls arranged on the base.

7. The coordinate alignment tool for the measuring X-ray CT apparatus and the coordinate measuring device according to claim 1, wherein the fixer is one of a chuck, an adhesive, or a double-sided adhesive tape.

* * * * *